United States Patent
Endou et al.

(10) Patent No.: US 7,521,570 B2
(45) Date of Patent: Apr. 21, 2009

(54) MEDICINAL COMPOSITIONS CONTAINING 6-HYDROXYBENZBROMARONE OR SALTS THEREOF

(75) Inventors: Hitoshi Endou, Kanagawa (JP); Toshihiro Oikawa, Chiba (JP)

(73) Assignees: Torli Pharmaceutical Co., Ltd., Tokyo (JP); Human Cell Systems, Inc., Tokyo (JP)

( * ) Notice: Subject to any disclaimer, the term of this patent is extended or adjusted under 35 U.S.C. 154(b) by 0 days.

(21) Appl. No.: 11/628,918

(22) PCT Filed: Jun. 10, 2005

(86) PCT No.: PCT/JP2005/010671

§ 371 (c)(1),
(2), (4) Date: Dec. 6, 2006

(87) PCT Pub. No.: WO2005/121112

PCT Pub. Date: Dec. 22, 2005

(65) Prior Publication Data

US 2007/0185195 A1     Aug. 9, 2007

(30) Foreign Application Priority Data

Jun. 10, 2004   (JP) ............................. 2004-172456

(51) Int. Cl.
*C07D 307/93*    (2006.01)
*A61K 31/34*     (2006.01)

(52) U.S. Cl. ..................................... 549/462; 514/469
(58) Field of Classification Search .................. 549/462; 514/469
See application file for complete search history.

(56) References Cited

OTHER PUBLICATIONS

Walter-Sack et al. European Journal of Medical Research (1998), 3(1/2), 45-49.*
Walter-Sack et al., European Journal of Medical Research, 1:16-20 (1995).
De Vries et al., Zenobiotica, 23(12):1435-1450 (1993).
Deltour et al., Archives Internationales de Pharmacodynamie et de Therapie, 165(1):25-30 (1967).

* cited by examiner

*Primary Examiner*—D. Margaret Seaman
*Assistant Examiner*—Nizal S Chandrakumar
(74) *Attorney, Agent, or Firm*—Peter F. Corless; Christine C. O'Day; Edwards Angell Palmer & Dodge LLP

(57) ABSTRACT

To provide highly safe therapeutic or preventive agents for hyperuricemia, more specifically uricosuric agents, which have potent uricosuric effect and do not cause grave hepatic disorder. Medicinal compositions for the treatment or prevention of hyperuricemia or diseases caused by hyperuricemia, which contain 6-hydroxybenzbromarone or salts thereof, and pharmaceutically acceptable carriers; uricosuric agents, xanthine oxidase inhibitors, and inhibitors against the uptake of uric acid in kidney, which contain 6-hydroxybenzbromarone or salts thereof; and a process for the production of 6-hydroxybenzbromarone.

1 Claim, 4 Drawing Sheets

MEDICINAL COMPOSITIONS CONTAINING 6-HYDROXYBENZBROMARONE OR SALTS THEREOF

TECHNICAL FIELD

The present invention relates to a medical composition containing 6-hydroxybenzbromarone or salt thereof, and a pharmaceutically acceptable carrier, and more particularly to a medical composition for treatment and prevention of hyperuricemia or disorders resulting therefrom containing 6-hydroxybenzbromarone or salt thereof, and a pharmaceutically acceptable carrier, and to uricosuric agent, xanthine oxidase inhibitor and inhibitor against the uptake of uric acid in kidney containing 6-hydroxybenzbromarone or salt thereof. Further, the present invention relates to a method for manufacturing 6-hydroxybenzbromarone including brominating 2-ethyl-6-hydroxy-3-(p-hydroxy-benzoyl)-benzofuran (hydroxy groups thereof may be protected as necessary) using a brominating agent and then deprotecting protective groups of hydroxy groups.

BACKGROUND ART

Gout is severe disease accompanying various symptoms such as arthritis (gout attack), gouty tophus, urinary calculi or the like. Gout is deeply associated with lifestyle habit, and in Japan, this disease was rarely found before 1960, but increased with high-growth of the economy and at present, it is said that more than six hundred thousand patients are suffering from this disease. Conventionally, age of onset of gout was in fifties, but at present, a peak age thereof onset is moved to thirties, and age of onset tends to shift to younger generation. Further, hyperuricemia that is a basic pathology of gout has been increasing. It is reported that when serum uric acid level is elevated, risk for ischemic heart disease as well as gout is increased.

Pathologic conditions of hyperuricemia fall into two categories; an uric acid production promotion type and an uricosuric suppression type. Ratio of each of types among all patients with hyperuricemia is said to be approximately 20% for uric acid production promotion type, approximately 60% for uricosuric suppression type, and approximately 20% for combination of the two. At present, use of allopurinol that is xanthine oxidase inhibitor is recommended for the former and benzbromarone that is uricosuric agent is recommended for the latter. At least 20 years have passed since both drugs were released and for allopurinol, side effects such as hepatic disorder (including fulminant hepatitis), bone-marrow suppression, severe dermatitis or the like are reported so far; for oxypurinol that is a metabolite of allopurinol, it is reported that blood disorder and hepatic disorder are caused in dialysis patients due to accumulation of this drug at high-level in the body. For benzbromarone, hepatic disorder (including fulminant hepatitis) is reported. In view of the foregoing, developments of new drugs with the least side effects have been desired.

For uricosuric agent, those in which benzofuran skeleton of benzbromarone is left and side-chain portions are chemically modified in various ways are reported (see Patent Documents 1 to 4). Further, for uricosuric agent one using a compound having nonpeptide angiotensin II receptor antagonistic action (see Patent Document 5), one using dihydropyridine derivatives (see Patent Document 6), one using hydantoin derivatives (see Patent Document 7), one using biaryl compounds or diaryl ether compounds (see Patent Document 8), or the like are reported.

Besides, for xanthine oxidase inhibitor for suppressing the production of uric acid, one using pyrazolo-triazine derivatives (see Patent Document 9), one using 3-phenylpyrazole compounds (see Patent Document 10), one using 1-phenylpyrazole compounds (see Patent Document 11), one using *Filipendula ulmaria* that is rosaceous perennial (General name; meadowsweet), one using quercetin-4'-glycoside and quercetin-3-glycoside isolated therefrom (see Patent Documents 12 and 13), one using 2-phenylthiazole derivatives (see Patent Document 14), one using plant body selected from *Origanum valgare, Mosla chinensis, Elsholtzia ciliata, Elsholtzia patrini, Elsholtzia splendens, Melissa officinalis, Rosmarinus officinalis, Mentha spicata, Mentha x piperita, Satureja montana, Piper betle* and *Ehretia microphylla,* and/or extracts of the plant body (see Patent Document 15), or the like are reported.

In addition, as new type of therapeutic agent for hyperuricemia, one using a insulin resistance improved substance such as thiazolidinedione compounds or the like (see Patent Document 16), one relating to prophylactic and therapeutic agent for hyperuricemic disorder containing monoene acid having a carbon number of 20 and/or derivative thereof, and monoene acid having a carbon number of 22 and/or derivative thereof as the active ingredient (see Patent Document 17), one relating to uric acid level depressant containing extracts from ginkgo biloba as the active ingredient (see Patent Document 18), one relating to treatment of hyperuricemia or prophylactic composition containing chondroitin sulfuric acid protein conjugate as the active ingredient (see Patent Document 19) or the like are reported.

Of them, several novel xanthine oxidase inhibitors, domestically and abroad, are already in their development stage, while for uricosuric agents, no movement of the development has been seen worldwide, and for the sake of improvements of QOL of patients with hyperuricemia, developments of new uricosuric agents with the least side effects have been desired.

In the meantime, benzbromarone represented by the following formula is;

[Chemical formula 1]

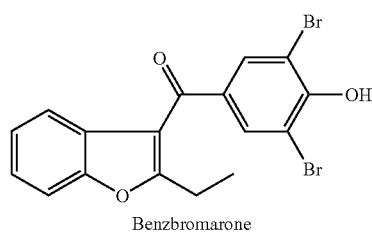

Benzbromarone is one type of benzofuran derivatives, and has been used extensively for long years due to its potent uricosuric effect. As for drug metabolism of benzbromarone, in the report (see Non-patent Document 1) for human patients disclosed in 1972, it was considered that benzbromarone is debromination metabolized in the liver, and is metabolized to bromobenzarone lacking one bromine or to benzarone lacking two bromine. However, later research revealed that metabolic products of benzbromarone is not debrominated substances, but primarily hydroxides in which first position or sixth position of benzofuran ring is hydrated (see Non-patent Document 2 to 6). It has also been suggested that as for persistence of uricosuric action of benzbromarone, metabolic products in the blood may be involved (see Non-patent Document 5).

Further, onset of severe hepatic disorder in patients taking benzofuran derivatives such as benzbromarone, benzarone, benziodarone or the like has been reported, and possibility that metabolic products common to these drugs might be associated with manifestation of hepatic disorder has been pointed out. Particularly, since benzarone is a dehalogenated substance of benziodarone and benzbromarone, the possibility that benzarone itself may trigger hepatic disorder has not been denied completely yet.

As discussed above, many researches have been made on metabolic products of benzofuran derivatives such as benzbromarone, benzarone, benziodarone or the like and side effects thereof, therapeutic agent or prophylactic agent for hyperuricemia which does not cause severe hepatic disorder, is highly safe, and has potent uricosuric action have not been developed at the present moment.

Patent Document 1: Japanese Patent Application Laid-Open (JP-A) No. 59-73579
Patent Document 2: JP-A-1-216984
Patent Document 3: JP-A-3-261778
Patent Document 4: JP-A-6-184132
Patent Document 5: JP-A-5-25043
Patent Document 6: JP-A-5-279255
Patent Document 7: WO 97/02033
Patent Document 8: JP-A-2000-1431
Patent Document 9: JP-A-6-316578
Patent Document 10: JP-A-10-310578
Patent Document 11: WO 98/18765
Patent Document 12: JP-A-2002-121145
Patent Document 13: JP-A-2003-171283
Patent Document 14: JP-A-2002-105067
Patent Document 15: JP-A-2003-252776
Patent Document 16: JP-A-11-255669
Patent Document 17: JP-A-2001-278786
Patent Document 18: JP-A-2002-212085
Patent Document 19: JP-A-2003-335698
Non-patent Document 1: Broekhuysen, J., et al., Eur. J. Clin. Pharmacol., 4, 125-130 (1972)
Non-patent Document 2: Walter-Sack, I., et al., Eur. J. Clin. Pharmacol., 39, 577-581 (1990)
Non-patent Document 3: De Vries, J. X., et al., Clin. Investig., 71, 947-952 (1993)
Non-patent Document 4: De Vries, J. X., et al., Xenobiotica, 23, 1435-1450 (1993)
Non-patent Document 5: Walter-Sack, I., et al., Eur. J. Med. Res., 1, 16-20 (1995)
Non-patent Document 6: Walter-Sack, I., et al., Eur. J. Med. Res., 3, 45-49 (1998)

DISCLOSURE OF THE INVENTION

Problems to be Solved by the Invention

The object of the present invention is to provide a therapeutic agent or a prophylactic agent which has potent uricosuric action, does not cause severe hepatic disorder, and is highly safe, and particularly to provide a uricosuric agent.

Means for Solving by the Problems

It is reported that benzbromarone is subjected to two-stage metabolism, that is to say, oxidation and conjugation, in the liver. Metabolism of a first layer is oxidation reaction by P450 that is a drug-metabolizing enzyme, and benzbromarone is converted primarily to 6-hydroxybenzbromarone by this reaction. Metabolism of a second layer is conjugation reaction by conjugation enzyme, and 6-hydroxybenzbromarone forms a conjugate by this reaction and is excreted in bile or urine. It is inferred that side effects by benzbromarone are attributable to the fact in that unknown toxic metabolites are produced by the reaction in the first layer.

The present inventors then focused attention on 6-hydroxybenzbromarone that is a metabolic product of the first layer of benzbromarone. The inventors then considered that, if this substance has uricosuric activity, production of unknown toxic metabolites in the reaction in the first layer of benzbromarone could be suppressed and development of auricosuric agent with the least side effects and higher safety would be possible. Further they investigated bioactivity of 6-hydroxybenzbromarone and found that 6-hydroxybenzbromarone, which has been unnoticed so far, has potent inhibitory action against uptake of uric acid in the kidney and that it has xanthine oxidase inhibitory action similar to that of oxypurinol that is a metabolic product of allopurinol, thereby resulting in the present invention.

The present invention relates to a medical composition containing 6-hydroxybenzbromarone or salt thereof, and a pharmaceutically acceptable carrier, and more particularly to a medical composition that is a therapeutic agent and a prophylactic agent for hyperuricemia or disorders resulting therefrom.

The present invention relates to a uricosuric agent containing 6-hydroxybenzbromarone or salt thereof. Further, the present invention relates to a xanthine oxidase inhibitor containing 6-hydroxybenzbromarone or salt thereof. Moreover, the present invention relates to an inhibitor for inhibiting uptake of uric acid in the kidney containing 6-hydroxybenzbromarone or salt thereof.

The present invention relates to the use of 6-hydroxybenzbromarone or salt thereof for manufacturing a medical composition for treatment and prevention of hyperuricemia or disorders resulting therefrom.

Further, the present invention relates to a method of treating or preventing hyperuricemia or disorders resulting therefrom including administering a medical composition containing an effective amount of 6-hydroxybenzbromarone or salt thereof, and pharmaceutically acceptable carrier to patients with hyperuricemia or disorders resulting therefrom.

Further, the present invention relates to a method for manufacturing 6-hydroxybenzbromarone including brominating 2-ethyl-6-hydroxy-3-(p-hydroxy-benzoyl)-benzofuran (hydroxy groups thereof may be protected as necessary) using a brominating agent and then deprotecting protective groups of hydroxy groups.

6-hydroxybenzbromarone according to the present invention is 2-ethyl-6-hydroxy-3-(3',5'-dibromo-4'-hydroxy-benzoyl)-benzofuran represented by the following chemical formula:

[Chemical formula 2]

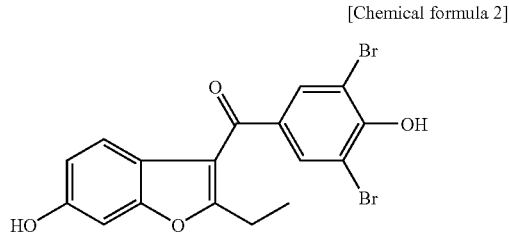

As for salts of 6-hydroxybenzbromarone according to the present invention, pharmaceutically acceptable salts are preferred and, for example, sodium salt, potassium salt or the like are mentioned.

6-hydroxybenzbromarone according to the present invention can be chemically synthesized by various methods and can be produced, for example, by brominating 2-ethyl-6-hydroxy-3-(p-hydroxy-benzoyl)-benzofuran in which hydroxy group is protected as necessary, using brominating agent such as N-bromosuccinimide and then deprotecting the protective groups of the hydroxy groups. As for protective group of hydroxy group, various protective groups known in the art of peptide chemistry may be used, while etherification by lower alkyl such as methyl group, ethyl group, t-butyl group or the like and esterification by lower acyl group such as methylcarbonyl group, ethylcarbonyl group, t-butylcarbonyl group or the like are mentioned.

2-ethyl-6-hydroxy-3-(p-hydroxy-benzoyl)-benzofuran that is used as the raw material can be produced by reacting 2-ethyl-6-hydroxy-benzofuran in which hydroxy group is protected as necessary, with a reactive derivative such as acid halide of p-hydroxy-benzoic acid. 2-ethyl-6-hydroxy-benzofuran used as the raw material in this case can be produced by reduction of carbonyl group of 2-acetyl-6-hydroxy-benzofuran in which hydroxy group is protected as necessary.

As for preferred example of producing 6-hydroxybenzbromarone according to the present invention, it can be produced as follows. That is, for example, 2-acetyl-6-hydroxy-benzofuran is reduced using hydrazine to obtain 2-ethyl-6-methoxy-benzofuran, which is then reacted with acid chloride of 4-methoxy-benzoic acid under the presence of tin tetrachloride to yield 2-ethyl-6-methoxy-3-(p-methoxy-benzoyl)-benzofuran. And then methoxy group of benzoyl group is selectively deprotected under the presence of ethane thiol sodium salt to yield 2-ethyl-6-methoxy-3-(p-hydroxy-benzoyl)-benzofuran, which is then brominated by sodium-N-bromosuccinimide under the presence of dimethyl sulfide to obtain 2-ethyl-6-methoxy-3-(3',5'-dibromo-4'-hydroxy-benzoyl)-benzofuran, and then methoxy group at sixth place is deprotected under the presence of aluminum chloride.

6-hydroxybenzbromarone and salts thereof according to the present invention may take the form of a medical composition together with ordinary pharmaceutically acceptable various carriers. As pharmaceutically acceptable carriers, diluting agent, binding agent, disintegrating agent, lubricant, diluent or the like used ordinarily for drug formulation are mentioned. The medical composition according to the present invention may take various administration routes according to the therapeutic purpose and may be administered by, for example, oral route, transmucosal route, parenteral route or the like. Depending on these administration routes, they are formulated into tablets, granules, capsules, powders, solutions, suspensions, emulsions, suppositories, injections (liquid medicine, suspension or the like) or the like. When formulating into orally administered drugs such as tablets, granules or the like, as for carriers, for example, diluting agents such as lactose, saccharose, sodium chloride, glucose, urea, starch, calcium carbonate, kaolin, crystalline cellulose, silic acid or the like; binding agents such as glucose solution, starch solution, gelatin solution, carboxymethylcellulose, shellac, methylcellulose, potassium phosphate, polyvinylpyrrolidone or the like; disintegrating agents such as starch, alginate sodium, powdered agar, sodium hydrogen carbonate, calcium carbonate, lactose or the like; and lubricants such as purified talc, stearate, powdered boric acid, polyethylene glycol or the like are mentioned. Using these carriers, they may be formulated into various dosage forms by known methods in the art.

The amount of 6-hydroxybenzbromarone or salts thereof contained in the medical composition according to the present invention is selected from a wide range, whereas it may normally be from 1 to 80 wt % of whole composition, approximately from 10 to 70 wt %.

A dose of the medical composition according to the present invention may be selected appropriately depending on age and sex of the patient, symptoms and severity of the disorder, whereas it is normally from 0.01 to 500 mg/kg of body weight/day, preferably from 0.1 to 100 mg, from 0.1 to 50 mg, and it is preferable to administer it from two to four times per day.

6-hydroxybenzbromarone or salts thereof according to the present invention have uricosuric effect and xanthine oxidase inhibitory action and are effective for treatment and prevention of hyperuricemia or disorders resulting therefrom. As for disorders resulting from hyperuricemia, gout, uric acid (uric acid salt) crystal storage disease, arthritis (gout attack), urinary calculus, ischemic heart disease or the like are mentioned. Further, treatment and prevention of various complications such as obesity, hypertension, hyperlipemia or the like resulting from these disorders are encompassed.

Although uricosuric agent, xanthine oxidase inhibitor and inhibitor against the uptake of uric acid in the kidney are preferably used as the medical composition for their intended purposes, they are not limited thereto, and use as the reagent for use in various tests and use as food additives to be added to foods are encompassed.

As for the inhibitor for uptake of uric acid in the kidney according to the present invention, more specifically, suppression of uptake by URAT1 (Atsushi, E., et al., Nature, 417 (6887), 447-453 (2002)) that is a uric acid specific transporter associated with uptake of uric acid in the kidney is mentioned.

Next, actions of 6-hydroxybenzbromarone and salts thereof according to the present invention will be explained hereafter.

The inventors of the present invention investigated actions of 6-hydroxybenzbromarone and benzbromarone used conventionally as the therapeutic agent for hyperuricemia against URAT1 (Atsushi, E., et al., Nature, 417 (6887), 447-452 (2002)) that is a uric acid specific transporter associated with uptake of uric acid in the kidney.

cDNA of URAT1 was introduced into MDCK cells and stably expressing cells (MDCK-URAT1) were created. Using this cell, a solution containing 6-hydroxybenzbromarone or benzbromarone of various concentrations was added to Dulbecco's modified PBS solution containing 100 μM of [$^{14}$C] uric acid, and then dpm of [$^{14}$C] uric acid taken into the cell was counted using a liquid scintillation counter. Experiments are carried out each three times and level of $IC_{50}$ was analyzed by profit.

Results of 6-hydroxybenzbromarone and benzbromarone are shown in FIG. 1 and FIG. 2 in the form of graphs, respectively. The vertical axis of FIG. 1 and FIG. 2 represents the amount of uric acid uptake (pmol/mg protein/min) and horizontal axis represents concentration (μM) for each. In FIG. 1, level of $IC_{50}$ is 0.13 μM and in FIG. 2, level of $IC_{50}$ is 0.031 μM.

Results of experiments, which were carried out three times, revealed that both 6-hydroxybenzbromarone and benzbromarone inhibit the uptake of uric acid in concentration dependent fashion, and level of $IC_{50}$ of 6-hydroxybenzbromarone after three times experiments is 0.20±0.06 μM and level of $IC_{50}$ of benzbromarone is 0.0345±0.003 μM. This reveals that 6-hydroxybenzbromarone, same as benzbromarone, inhibits the uptake of uric acid in concentration dependent manner and has uricosuric action. Further, it has been identified that although its intensity is approximately ⅙ of that of benzbromarone, it has considerably potent uricosuric action.

Subsequently, xanthine oxidase inhibitory activity of 6-hydroxybenzbromarone was investigated. Activity of xanthine oxidase derived from bovine milk was checked as follows: Using 100 μM of xanthine as the substrate, and using a system for measuring chronologically the absorbance (292 nm) of urea generated at 37° C. in 1/15 M phosphate buffer solution (pH 7.4) in which 0.1 M phosphate buffer solution was diluted by half volume of water, inhibitory activity of 6-hydroxybenzbromarone or of oxypurinol that is a metabolic product of allopurinol was measured to analyze $IC_{50}$. As a result, $IC_{50}$ level of 6-hydroxybenzbromarone was 68 μm and that of oxypurinol was 13 μM. Consequently, it has been known that 6-hydroxybenzbromarone according to the present invention has inhibitory activity of xanthine oxidase approximately ⅕ of that of oxypurinol.

Next, clinical pharmacokinetic test was carried out for a case where single dose of benzbromarone was given to healthy male adult subjects. After administration, plasma concentration and urine concentration of 6-hydroxybenzbromarone or benzbromarone were determined using LC/MS/MS.

Results of plasma concentration of 6-hydroxybenzbromarone are shown in FIG. 3 and results of urine concentration of the same are shown in FIG. 4, respectively. The vertical axis of FIG. 3 represents plasma level (ng/mL) and the horizontal axis represents time elapsed (hour). Cross mark (x) by dotted line in FIG. 3 denotes 6-hydroxybenzbromarone case and white triangle mark (Δ) denotes benzbromarone case. The vertical axis of FIG. 4 represents concentration in the urine (ng/mL) and the horizontal axis represents time elapsed (hour).

As a result, plasma concentration of benzbromarone increased quickly after administration, decreased gradually, and eliminated 48 hours after administration. Meanwhile, 6-hydroxybenzbromarone was present in the plasma for longer time, detected as much as approximately 110 ng/mL on average even 72 hours after administration, and AUC also exhibited twice or higher level than that of benzbromarone. 6-hydroxybenzbromarone was detected as much as approximately 170 ng/mL on average even 72 hours after administration, while benzbromarone was detected little in the urine.

From above-mentioned findings, it became apparent that 6-hydroxybenzbromarone inhibits uptake of uric acid by transporter URAT1 as much as the same level of benzbromarone and it has been shown that uricosuric effects are accomplished with a similar manner as benzbromarone. It has been shown that since URAT1 is present at luminal side of epithelial cell of the renal tubule, 6-hydroxybenzbromarone in the urine contributes to inhibition of resorption of uric acid by URAT1.

Besides, according to the results of clinical pharmacokinetic test of benzbromarone for human, benzbromarone was detected little in the urine from healthy male adults who underwent single-dose of benzbromarone, whereas high level of 6-hydroxybenzbromarone was detected in the urine till 72 hours after administration.

Moreover, since it is revealed that 6-hydroxybenzbromarone inhibits xanthine oxidase, it is shown that 6-hydroxybenzbromarone is also effective for uric acid production promotion type pathologic conditions.

Advantages Of The Invention 6-hydroxybenzbromarone or salt thereof according to the present invention has xanthine oxidase inhibitory action as well as potent uricosuric actions and are effective as the active ingredient for treatment and prevention of hyperuricemia and disorders resulting from hyperuricemia. At the same time, 6-hydroxybenzbromarone or salt thereof according to the present invention is hardly subjected to metabolism in the liver and are free from side effects such as severe hepatic disorder as encountered by conventional uricosuric agent, capable of maintaining the blood concentration at higher level for long period of time. Further toxicity thereof is low, and higher safety factor may be used, and consequently, safety thereof is extremely high. The medical composition according to the present invention is to provide a therapeutic agent or a prophylactic agent for hyperuricemia which has potent uricosuric action, does not cause severe hepatic disorder, and has higher safety, and more specifically, to provide a uricosuric agent.

BEST MODE FOR CARRYING OUT THE INVENTION

Figure 1:
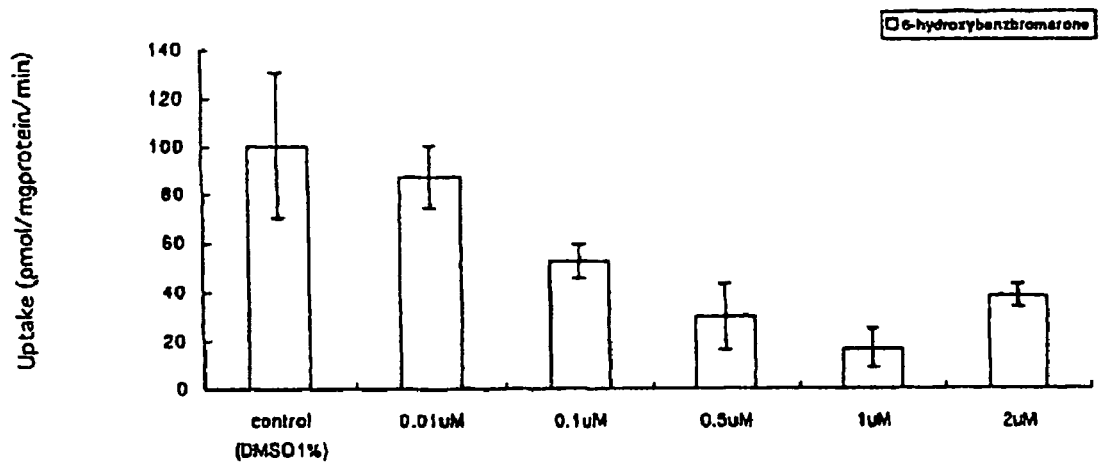
FIG. 1 is a graph showing experimental results of uptake inhibitory action of 6-hydroxybenzbromarone according to the present invention in uptake of uric acid by URAT1.

The present invention will be explained hereafter in more detail referring to examples, but the present invention is not limited by any of these examples.

EXAMPLE 1

Manufacturing of 6-hydroxybenzbromarone (1) Preparation of 2-ethyl-6-methoxybenzofuran Hydrazine (4.11 g, 69.4 mmol, up to 55%, Aldrich) was added to diethylene glycol solution of 2-acetyl-6-methoxybenzofuran (3.30 g, 17.3 mmol). The mixture was heated to a temperature of 190° C. and stirred for 10 min. After cooled down to room temperature, potassium hydroxide (2.92 g, 52.1 mmol) was added, stirred in a range of 120° C. to 130° C. for 6 hours. Following this, the reaction solution was poured into water, extracted by dichloromethane, dried over $MgSO_4$, and was concentrated under reduced pressure. Oil residue was purified by HPLC (silica gel, $CHCl_3$) and target product (2.98 g, 16.9 mmol, 97%) was obtained.

(2) Preparation of 3-(p-anisoyl)-2-ethyl-6-methoxy-benzofuran

Dried carbon disulfide solution (20 ml) of 2-ethyl-6-methoxy-benzofuran (2.76 g, 15.6 mmol) and p-anisoyl chloride (3.48 g, 20.3 mmol) was cooled on ice, to which tin chloride (IV) was dropped (5.25 g, 20.3 mmol) while stirring. The mixture was stirred at a temperature in a range of 5 to 10° C. for 3 hours and then poured into water. The organic layer was washed with diluted hydrochloric acid and water, dried over $MgSO_4$, and concentrated under reduced pressure. Crude product thereof was purified by HPLC (silica gel, ethyl acetate: hexane=2:8) and a target product in pale yellow oily state (2.98 g, 9.60 mmol, 58%) was obtained.

(3) Preparation of 2-ethyl-3-(p-hydroxy benzoyl)-6-methoxy benzofuran

Dimethyl formamide solution of 3-(p-anisoyl)-2-ethyl-6-methoxybenzofuran (2.39 g, 7.7 mmol) and ethanethiolic sodium salt (971 mg, 11.5 mmol) was stirred at 80° C. for 4 hours. This reaction was completed using $NH_4Cl$ solution and extraction was performed with chloroform. The extract was washed with water and saline solution, dried over $Ma_2SO_4$, and concentrated under reduced pressure. The residue was purified by HPLC (silica gel, ethyl acetate:hexane=2:8) and a target product (2.28 g, 7.70 mmol, 100%) was obtained.

(4) Preparation of 6-methoxy benzbromarone

To dichloromethane solution of N-bromosuccinimide (12.0 g, 67.5 mmol) was added dimethylfide (5.0 ml, 68 mmol) under ice bath cooling by ice and salt. After stirred for 10 min, dichloromethane solution of 2-ethyl-3-(p-hydroxy benzoyl)-6-methoxy benzofuran (2.00 g, 6.75 mmol) was added at the same temperature. The mixture was stirred at room temperature for 15 hours. Water was added to this reaction solution, organic layer was isolated, washed with water and saline solution, dried over $MgSO_4$, and concentrated under reduced pressure. The residue thereof was purified by HPLC (chloroform) and a target product (1.70 g, 3.74 mmol, 55%) was obtained.

(5) Preparation of 6-hydroxybenzbromarone

To $AlCl_3$ (2.346 mg, 17.6 mmol) was dropped 7 ml of ethanethiol being cooled in ice bath. This solution was added to dichloromethane solution (35 ml) of 6-methoxy benzbromarone (1.70 g, 3.74 mmol). After stirred at the same temperature for 10 min, water was added and 1N HCl solution was added. Its organic layer was isolated and aqueous layer was extracted twice by ethyl acetate. The organic layer thus obtained was washed with saline solution, dried over $MgSO_4$, and concentrated under reduced pressure. The residue was purified by HPLC (silica gel, $CHCl_3$: MeOH=30:1), recrystallized from isopropyl ether, and a target product 1.00 g (2.35 mmol, 63%) was obtained.

Figure 5:
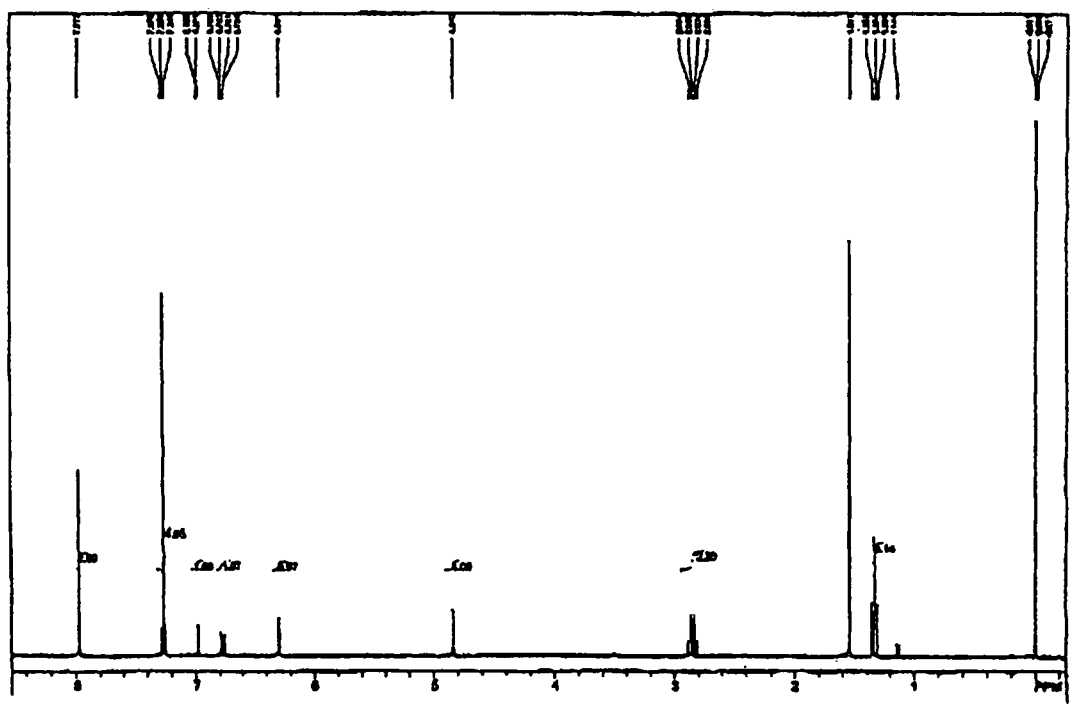
FIG. 5 is a chart showing $^1$H-NMR (300 MHz, bichloroform) of 6-hydroxybenzbromarone according to the present invention.

The purity of 6-hydroxybenzbromarone thus obtained was determined by HPLC to be 99.8%. FIG. 5 shows a chart of $^1$H-NMR(300 MHz, bichloroform) thereof.

EXAMPLE 2 cDNA of URAT1 which was integrated into mammal expression vector pcDNA3.1, or pcDNA3.1 was gene transfected to MDCK cells to create stably expressing cells (MDCK-URAT1) and mock cells.

This MDCK-URAT1 was cultured in the minimal essential medium containing 5% fetal bovine serum and 400 µg/mL geneticin, cells were placed in 24-well dish (as many as $10^5$ cells per one well) and cultured for 2 days. After that, it was washed with Dulbecco's modified PBS and subjected to pre-incubation in the Dulbecco's modified PBS solution for 10 min.

Following this, a solution containing 6-hydroxybenzbromarone or benzbromarone having various concentrations was added to the Dulbecco's modified PBS solution containing 100 µM [$^{14}$C] uric acid, and incubated at 37° C. for 2 min. After that, it was washed with Dulbecco's modified PBS solution three times and cells were collected by 0.1N NaOH. Scintillation cocktail was then added to count dpm of [$^{14}$C] uric acid being taken in cells by liquid scintillation counter. Values of $IC_{50}$ were analyzed by profit.

Figure 2:
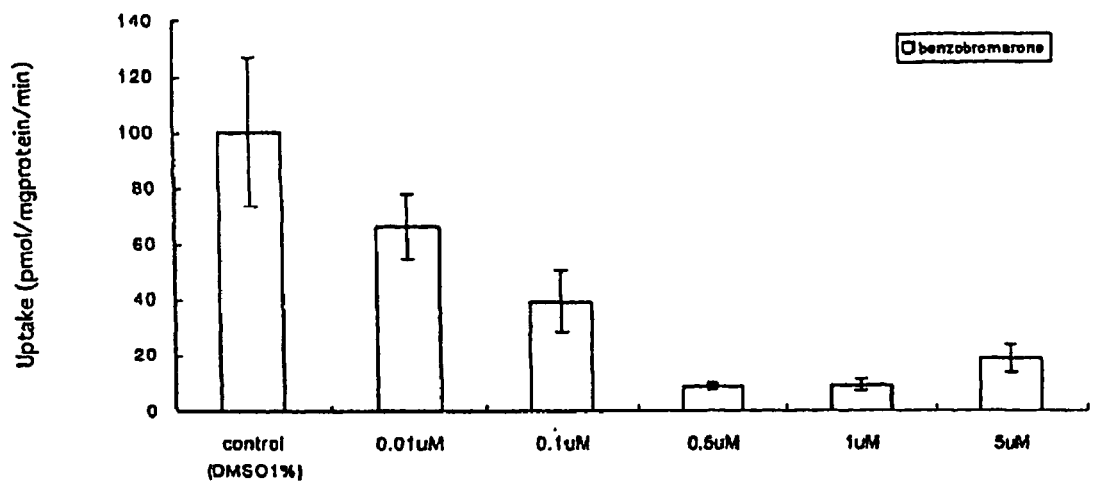
FIG. 2 is a graph showing experimental results of uptake inhibitory action of benzbromarone in uptake of uric acid by URAT1.

Results obtained are shown in FIG. 1 and FIG. 2. Results of experiments, which was carried out three times, revealed that both 6-hydroxybenzbromarone and benzbromarone inhibits the uptake of uric acid in concentration dependent fashion, and level of $IC_{50}$ of 6-hydroxybenzbromarone after three times experiments is 0.20±0.06 µM and level of $IC_{50}$ of benzbromarone is 0.0345±0.003 µM.

EXAMPLE 3

Activity of xanthine oxidase derived from bovine milk was analyzed as follows. Using 100 µM of xanthine as the substrate, and using a system for measuring chronologically the absorbance (292 nm) of urea generated at 37° C. in 1/15 M phosphate buffer solution (pH 7.4) in which 0.1 M phosphate buffer solution was diluted by half volume of water, inhibitory activity of 6-hydroxybenzbromarone or of oxypurinol was measured at concentrations of 0.0 µM, 0.1 µM, 0.3 µM, 1.0 µM, 3.0 µM, 10.0 µM, 30.0 µM, 100 µM, and 300 µM to analyze $IC_{50}$.

As a result, $IC_{50}$ level of 6-hydroxybenzbromarone was 68 µm and that of oxypurinol was 13 µM.

EXAMPLE 4

For six healthy male subjects at ages 20 to 27, two tablets of Urinorm (registered trademark) (100 mg as benzbromarone) were administered single orally together with 180 mL of water in the fasted state, and thereafter, blood sample collection and urine collection were performed with lapse of time till 72 hours. For plasma and urine thus obtained, benzbromarone, 6-hydroxybenzbromarone, bromobenzarone and benzarone were determined using LC/MS/MS. Prior to the test, it was confirmed with six subjects that their CYP2C9 that is associated with metabolism of benzbromarone is free from gene mutation (CYP2C9*3)

Figure 3:
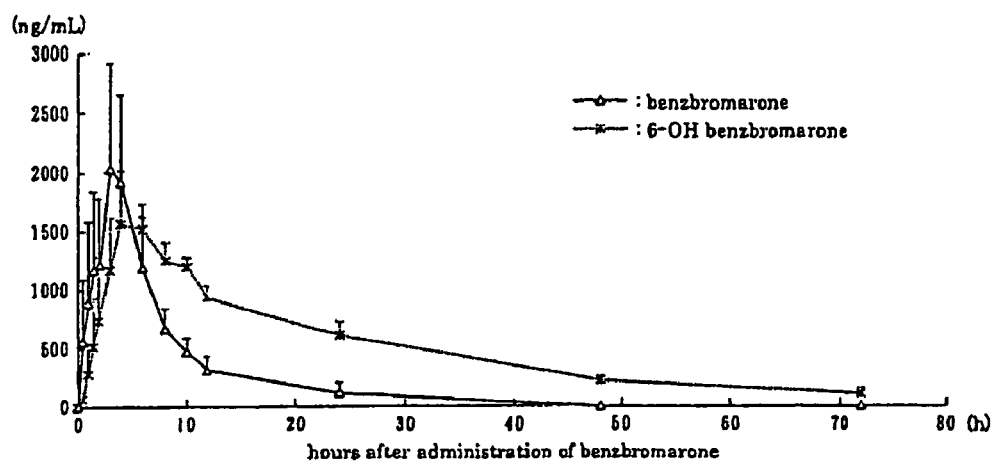
FIG. 3 is a graph showing plasma concentration (ng/mL) of 6-hydroxybenzbromarone (x mark by dotted line) and of benzbromarone (Δmark) in the results of clinical pharmacokinetic test of benzbromarone for healthy male adults.
Figure 4:
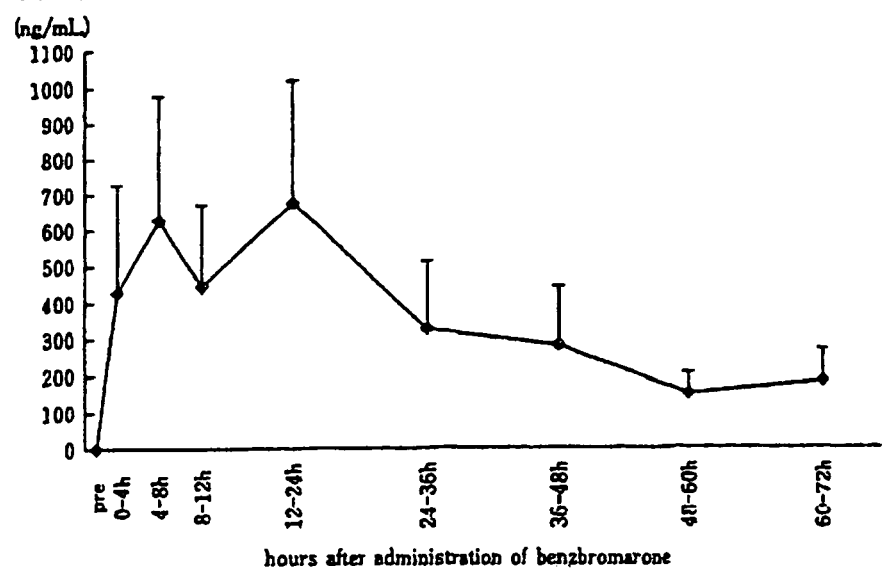
FIG. 4 is a graph showing urine concentration (ng/mL) of 6-hydroxybenzbromarone in the results of clinical pharmacokinetic test of benzbromarone for healthy male adults.

Results obtained are shown in FIG. 3 and FIG. 4.

EXAMPLE 5

Pharmacokinetic Test of Benzbromarone and 6-hydroxybenzbromarone Given in Single Dose Benzbromarone and 6-hydroxybenzbromarone were given respectively in single dose of 100 mg/kg to rats, which test revealed that $C_{max}$ and $AUC_{0-24hr}$ of benzbromarone were 90.19 µg/mL and 886.56 µg.hr/mL, respectively, while $C_{max}$ and $AUC_{0-24hr}$ of 6-hydroxybenzbromarone were 34.55 µg/mL and 290.80 µg·hr/mL, respectively.

As a result, it has been revealed that 6-hydroxybenzbromarone is absorbed favorably from the digestive tract into bloodstream, with a similar manner as benzbromarone. Therefore, it is considered that after administered orally, 6-hydroxybenzbromarone is absorbed into bloodstream, and is then excreted into urine, inhibits URAT1 present at luminal side of epithelial cell of the proximal renal tubule, thereby inhibiting resorption of uric acid.

EXAMPLE 6

Two-Week Repeated Dose Toxicity Test for Benzbromarone and 6-hydroxybenzbromarone Benzbromarone and 6-hydroxybenzbromarone were administered respectively to rats for 14 days at a dose of 100 mg/kg/day and it was found that liver weight increase (13.59 kg) was recognized in benzbromarone administration group, while no liver weight increase due to drug administration was realized (9.90 g) in 6-hydroxybenzbromarone administration group. Meanwhile, liver weight of rats in healthy control group was 9.43 g.

From results shown above, it is known that 6-hydroxybenzbromarone has fewer effects upon the liver than benzbromarone.

EXAMPLE 7

Results of Test of Action Mechanism by OAT4 (Organic Anion Transporter)

Figure 6:
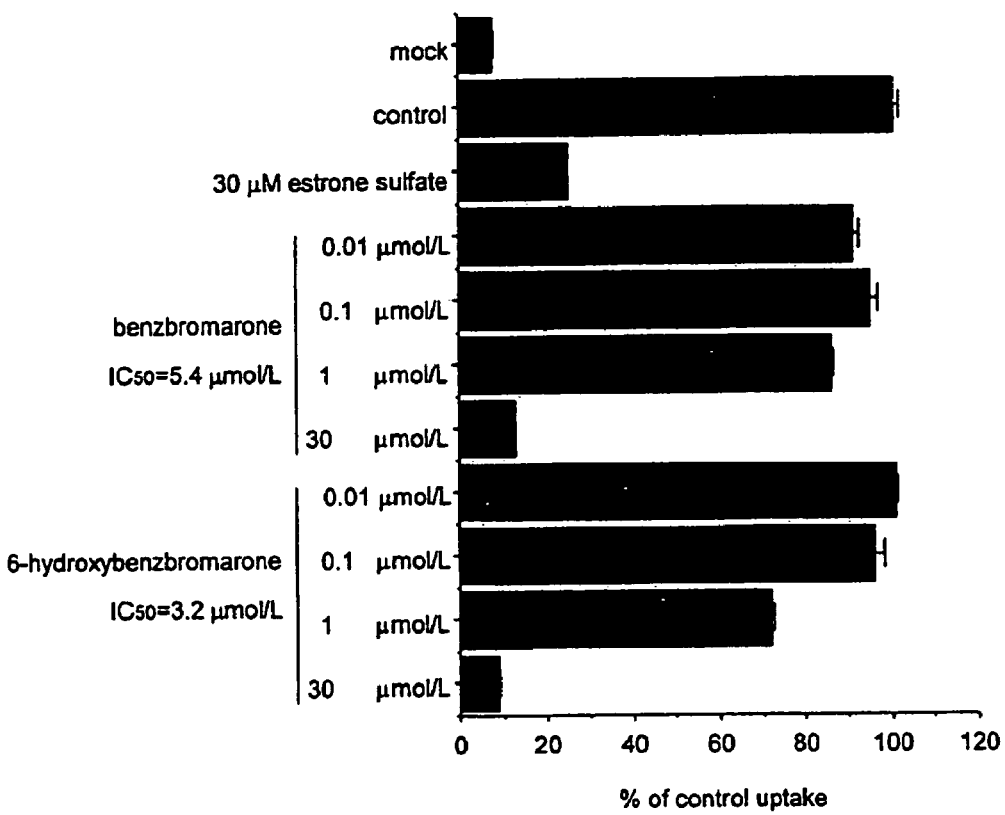
FIG. 6 shows results of measurement of inhibitory action of uptake of substrate $^3$H-estrone sulfate by human OAT4 (human organic anion transporter 4) in S2 cells in the presence of benzbromarone and 6-hydroxybenzbromarone.

OAT4 is an organic anion transporter which is present at luminal side membrane of the proximal renal tubule and takes organic anion such as uric acid into cells, and estrone sulfate is known as the typical substrate of this. In this regard, using S2 cells expressing OAT4, inhibitory action of uptake of estrone sulfate by OAT4 developed by benzbromarone and 6-hydroxybenzbromarone was checked by experiments. The amount of uptake of $^3$H-estrone sulfate (50 mmol/L) in the presence of benzbromarone and 6-hydroxybenzbromarone at 0.01 μmol/L, 0.1 μmol/L, 1 μmol/L, and 30 μmol/L, respectively was measured. Results are shown in FIG. 6 in the form of relative value while the amount of uptake of $^3$H-estrone sulfate in a case where nothing is present (control) is considered to be 100%.

As a result, it was found that 6-hydroxybenzbromarone inhibits the uptake of$^3$H-estrone sulfate at OAT4 in correlation with the dose and its $IC_{50}$ was 3.2 μmol/L. Further, the same of benzbromarone was 5.4 μmol/L.

As mentioned above, since 6-hydroxybenzbromarone has an inhibitory action against uptake of the substrate in OAT4, it is considered that 6-hydroxybenzbromarone inhibits in vivo resorption of uric acid by OAT4, thereby promoting excretion of uric acid.

EXAMPLE 8

Results of Test of Action Mechanism by OAT3 (Organic Anion Transporter)

Figure 7:
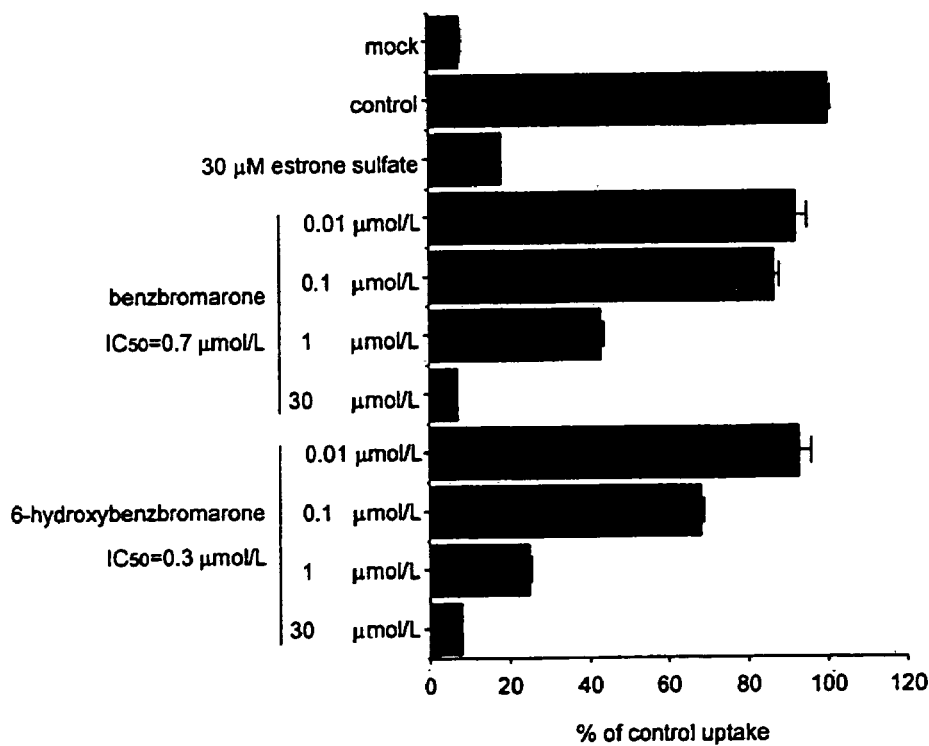
FIG. 7 shows results of measurement of inhibitory action of uptake of substrate $^3$H-estrone sulfate by human OAT3 (human organic anion transporter 3) in S2 cells in the presence of benzbromarone and 6-hydroxybenzbromarone.

OAT3 is an organic anion transporter which is present at basal-lateral (vascular side) membrane of the proximal renal tubule and takes organic anion such as uric acid into cells, and estrone sulfate is known as the typical substrate of this. Then, using S2 cells expressing OAT3, with a similar manner as Example 7, inhibitory action of uptake of estrone sulfate by OAT3 developed by benzbromarone and 6-hydroxybenzbromarone was checked by experiments. The amount of uptake of $^3$H-estrone sulfate (50 nmol/L) in the presence of benzbromarone and 6-hydroxybenzbromarone at 0.01 μmol/L, 0.1 μmol/L, 1 μmol/L, and 30 μmol/L, respectively was measured. Results are shown in FIG. 7 in the form of relative value while the amount of uptake of $^3$H-estrone sulfate for a case where nothing is present (control) is considered to be 100%.

As a result, it was found that 6-hydroxybenzbromarone inhibits the uptake of $^3$H-estrone sulfate by OAT3 in correlation with the dose and its $IC_{50}$ was 0.3 μmol/L. Further, the same of benzbromarone was 0.7 μmol/L.

As mentioned, 6-hydroxybenzbromarone has an inhibitory action against uptake of the substrate in OAT3.

Figure 8:
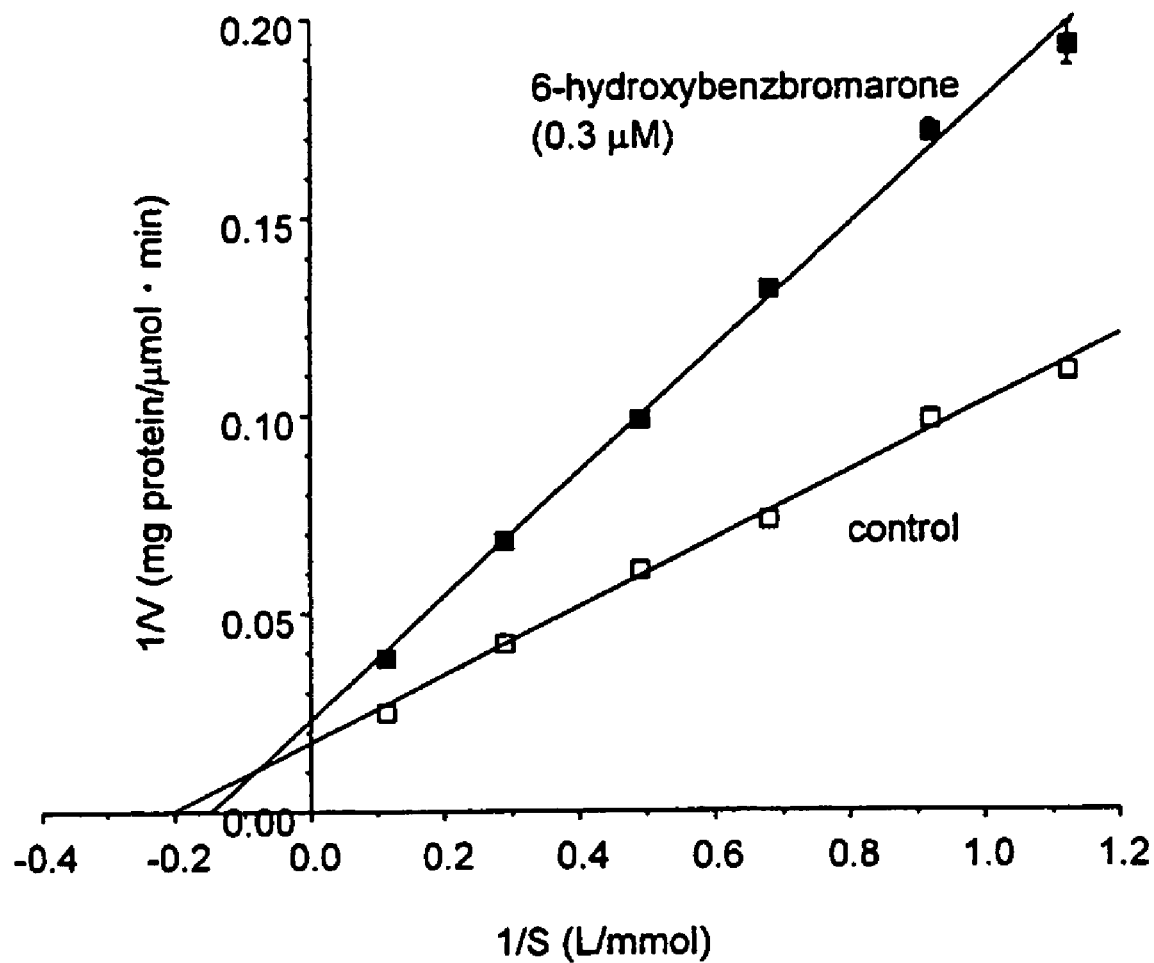
FIG. 8 shows results of analysis of constants (Ki-value) of inhibitory action of uptake of substrate $^3$H-estrone sulfate of 6-hydroxybenzbromarone in human OAT3 (human organic anion transporter 3).

Further, inhibitory action of 6-hydroxybenzbromarone in uptake of $^3$H-estrone sulfate by OAT3 was analyzed (Ki-value) Results are shown in FIG. 8. The horizontal axis of FIG. 8 represents 1/S (L/mmol) and the vertical axis represents 1/V (mg protein/μM/min), black square (■) denotes 6-hydroxybenzbromarone (0.3 μM) case and white square (□) denotes control. As a result, it was revealed that inhibitory style is a mixed type of competitive inhibition and noncompetitive inhibition. Ki-value was 1.0 μM (competitive inhibition) and 0.7 μM (noncompetitive inhibition), respectively.

It is therefore considered that a part of 6-hydroxybenzbromarone in the blood is taken into epithelial cell of the proximal renal tubule by OAT3 in competition with the substrate of OAT3 and inhibits URAT from cell inside, thereby inhibiting resorption of uric acid.

INDUSTRIAL APPLICABILITY

The present invention provides a therapeutic agent or prophylactic agent for hyperuricemia, which has potent uricosuric action, does not cause severe hepatic disorder, and has higher safety, and more specifically, uricosuric agent, which is extremely effective in the pharmaceutical industry.

The invention claimed is:

1. A medical composition containing 6-hydroxybenzbromarone or salt thereof, and a pharmaceutically acceptable carrier, wherein the medical composition is for therapeutic agent for hyperuricemia or disorders resulting therefrom.

* * * * *